United States Patent [19]

Eichel et al.

[11] Patent Number: 4,822,619
[45] Date of Patent: Apr. 18, 1989

[54] CONTROLLED RELEASE PHARMACEUTICAL PREPARATION CONTAINING A GASTROINTESTINAL IRRITANT DRUG

[75] Inventors: Herman J. Eichel; Brent D. Massman, both of Columbus, Ohio

[73] Assignee: Ionor, Inc., Dayton, Ohio

[21] Appl. No.: 16,134

[22] Filed: Feb. 18, 1987

[51] Int. Cl.$^4$ .................................. A61K 9/16
[52] U.S. Cl. .................... 424/492; 424/498; 424/490; 424/451
[58] Field of Search ............... 424/450, 492, 490, 498; 427/212

[56] References Cited

U.S. PATENT DOCUMENTS

| | | | |
|---|---|---|---|
| 3,903,255 | 9/1975 | Gusman et al. | 427/44 |
| 3,970,750 | 7/1976 | Brockemeyer et al. | 424/153 |
| 4,132,753 | 1/1979 | Blichare et al. | 424/498 X |
| 4,140,756 | 2/1979 | Gallian | 424/475 |
| 4,259,315 | 3/1981 | Lippmann et al. | 424/459 |
| 4,352,791 | 10/1982 | Zaffaroni et al. | 424/153 |
| 4,483,847 | 11/1984 | Augart | 424/470 |
| 4,574,080 | 3/1986 | Roswall et al. | 424/458 |
| 4,675,140 | 6/1987 | Sparks et al. | 427/240 |

OTHER PUBLICATIONS

Chemical Abstracts, vol. 104, 1986, pp. 56319, Abstract 56321p, Skoutakis, Vasilios A. Arcchiodo, Sajir K. et al.

*Primary Examiner*—Thurman K. Page
*Assistant Examiner*—L. R. Horne
*Attorney, Agent, or Firm*—Killworth, Gottman, Hagan & Schaeff

[57] ABSTRACT

A controlled release pharmaceutical preparation containing a micronized gastrointestinal irritant drug, such as potassium chloride, in a non-toxic protective balm. An irritant/balm admixture may be formed into microparticles. Alternatively, an irritant/balm admixture, may be used as the core for microcapsules. The microparticles or microcapsules may themselves be filled into a capsule or tabletted.

11 Claims, No Drawings

CONTROLLED RELEASE PHARMACEUTICAL PREPARATION CONTAINING A GASTROINTESTINAL IRRITANT DRUG

BACKGROUND OF THE INVENTION

The present invention relates to a controlled release product containing a pharmaceutical which is a gastrointestinal irritant. It also relates to a process for preparing such a product. More particularly, the present invention relates to micronized potassium chloride in a protective balm, preferably a microcapsule of micronized potassium chloride in a semi-solid balm, and a process for preparing the same.

It is well recognized that abnormally low levels of potassium chloride in the body may be caused by certain disease states or by the administration of certain therapeutic agents, such as, for example, corticosteroids, thiazide-type diuretics or other diuretics. The symptoms of this condition, hypokalemia, include muscular weakness and cardiac disturbances. Treatment of this condition normally comprises replacement of the potassium ion. In view of the fact that therapy with therapeutic agents such as those mentioned above may often be on a prolonged basis, it is often the case that potassium chloride replacement therapy must be maintained over extended periods of time.

The art is appraised of problems inherent with the administration of potassium chloride. Potassium chloride has been found to be irritating to the gastric mucosa and, therefore, be a potential source of ulceration. This has been shown to be true, for example, with enteric-coated potassium chloride tablets which have caused lesions of the lower bowel over a period of time in all probability due to irritation caused by the concentration of potassium chloride at the sites in the intestinal wall where such tablets dissolve.

There have been numerous attempts to formulate potassium chloride into dosage forms designed to overcome problems such as that described above with varying degrees of success. One approach to the formulation of potassium chloride is to compound it into a liquid formulation. Such a preparation would, for example, be advantageous in that it would be relatively free from the possibility of irritation caused by high concentration of potassium chloride at the site of dissolution of a tablet in the stomach or intestinal tract. A second obvious advantage of such liquid preparations would be acceptance by those patients who have difficulty swallowing a tablet.

However, liquid preparations have certain disadvantages. The most significant disadvantage of liquid potassium chloride preparations known heretofore is that, regardless of the type of liquid preparation or formulation thereof, such preparations do not have an acceptable taste. It is significant that attempts to date to market a liquid form of potassium chloride have not fared particularly well in comparison to commercial tablets or capsules due in the main to the inability of such liquid preparations to mask the salty, objectionable taste of potassium chloride.

For this reason, Ranucci in U.S. Pat. No. 4,259,323 proposes preparation of a better tasting, less irritating liquid emulsion of potassium chloride. Still, it is hard to effectively mask the taste of potassium chloride. Accordingly, solid potassium chloridecontaining tablets or capsules remain the dosable form of choice.

Another approach to the formulation of potassium chloride is to coat, encapsulate, or blend solid potassium chloride with a protective material. Sugar-coated tablets containing potassium chloride in a wax matrix are marketed as a slowly available potassium source. The use of a wax-like matrix is taught in Blichare U.S. Pat. No. 4,132,753, for example. Physicians Desk-Reference (1979), page 794, states "fewer bowel lesions are observed with wax-matrix tablets compared to enteric-coated potassium chloride products, but that there have been reports of upper gastrointestinal bleeding associated with the wax-matrix tablets. Use of these wax-coated products should be discontinued immediately and the possibility of bowel obstruction or perforation considered if severe vomiting, abdominal pain, distention or gastrointestinal bleeding occurs."

Because of the problem encountered with potassium chloride/wax-matrix tablets, Gallian in U.S. Pat. No. 4,140,756 proposes placing a permanent, erosion resistant polymeric film coating over a core of potassium chloride in a wax-like matrix. Release of the potassium chloride is to take place by way of diffusion of the gastric juices and intestinal fluids and potassium chloride through the polymeric film. A tablet of the type disclosed in the Gallian patent will result in controlled release of potassium chloride, so much so that large amounts of potassium chloride (preferably 900–1200 mg) are used. Large, concentrated amounts of potassium chloride, no matter how protected, still present the danger of ulceration. The tablets remain intact and may become lodged in the digestive tract, releasing large amounts of potassium chloride in a small localized area.

Gelatin capsules containing controlled release microencapsulated potassium chloride have also been proposed. See Lippmann U.S. Pat. No. 4,259,315. Testing of product produced in accordance with the Lippmann patent has shown that it is less ulcerogenic than solid enteric-coated or non-coated potassium chloride and has effects on the gut mucosa comparable to wax-matrix potassium chloride preparations. Lesion tests showed that enteric-coated potassium chloride caused marked ulceration in all instances while the product of Lippmann U.S. Pat. No. 4,259,315 produced only small local erosions. Wax-matrix potassium chloride released a considerable portion of potassium chloride contents in the stomach, caused more ulcers and erosions at that site than the product of the Lippman patent, but did not cause more distal lesions.

Most recently, it has been proposed that a wax-like material be mixed with a microencapsular material in preparing microencapsulated sustained release potassium chloride. See Roswall U.S. Pat. No. 4,574,080.

While such encapsulation systems show improved results over enteric-coated, uncoated, and wax-matrix potassium chloride preparations, they are not totally free from ulceration problems. Further improvement could be made.

Accordingly, the need exists for an improved system for controlled release of a gastrointestinal irritant drug such as potassium chloride.

SUMMARY OF THE INVENTION

That need is met by the present invention wherein micronized particles of a gastrointestinal irritant drug are admixed in a non-toxic protective balm and, then, formed into microcapsules or microparticles. The gastrointestinal irritant drug may be a micronized potassium salt, such as potassium chloride, preferably having an average particle size of less than 10 microns. Other solid, water soluble micronized gastrointestinal irritant drugs may also be used.

Thus, a key feature of the present invention is the ability of a protective balm to admix with micronized, solid gastrointestinal irritant drugs of any type so that the micronized particles are embedded in the balm and coated by it and yet the gastrointestinal irritant drug is dissolved in a controlled manner by the digestive fluids upon dispersion of the balm. In that manner, large concentrations of the gastrointestinal irritant drug are prevented from contacting the lining of the digestive tract for any significant periods of time.

Preferably the non-toxic protective balm is a digestible or non-digestible material, such as a vegetable fat, petroleum jelly, wax, lipid, glycerol derivative or mixtures thereof. Most preferably, the balm is a mixture of solid lipids or waxes and a relatively soft vegetable fat. The resulting semi-solid mixture has been found to disperse more readily in the digestive tract. Such semi-solid balms are, therefore, preferred. Further additives to the balm, such as surfactants and enzymes which aid in the dispersion, emulsification and digestion of the balm may be incorporated into the formula.

Such balm materials gradually spread and disperse in the digestive tract by reason of the body temperature, gastrointestinal motility and action of the digestive fluids. And yet, the balm protects the gastrointestinal irritant drug particles so that at any one time only a small amount of irritant is near the surface of the particle of irritant/balm admixture as it disperses in the digestive tract. As the balm is progressively emulsified, digested or dissolved, the micronized irritant particles near the surface of the balm are extracted from the balm by the digestive fluids. Thus, the irritant particles themselves seldom if ever come in contact with the walls of the digestive tract and there is little chance of localized areas of high irritant concentration being in contact with the lining of the digestive tract.

Microparticles of micronized irritant in the balm are readily dispersible in the digestive tract. Such microparticles may be prepared by forming a slurry of micronized irritant such as potassium chloride, in a balm material at a temperature above the melting point of the balm. The slurry is dispersed into a medium at a temperature below the melting point of the balm. The preferred mediums are gelatin solutions containing surfactants. Microparticles of the irritant/balm admixture are formed. The microparticles are separated from the medium. The microparticles are then washed, dried and sized. The preferred average diameter of such microparticles is between 100 and 1000 microns. Small microparticles of that size form an essentially free-flowing powder which can itself be filled into a gelatin capsule or formed into a tablet.

Alternatively, and preferably, a balm containing micronized irritant may be microencapsulated to form microcapsules of the same size as the microparticles discussed above. Such microcapsules may be produced by dispersing an admixture of micronized irritant and balm, at a temperature above the melting point of the balm, into a gelatin medium at a temperature below the melting point of the balm and, then, introducing a coacervating agent. The formed microcapsules are hardened, separated, dried and sized. They are then ready for use in a capsule or Table I as described above.

A microencapsular wall is particularly advantageous in that formation of microcapsules having a gelatin microencapsular wall and irritant/balm core permits even greater dispersion of the pharmaceutical after it enters the digestive tract and controles the release of the gastrointestinal irritant drug in the stomach. Again, the preferred average diameter of the microcapsules is between about 100 and 1000 microns. Small microcapsules of that size also form an essentially free-flowing powder which can be filled into a gelatin capsule. Alternatively, the microcapsules can be compressed into tablet form by known techniques.

In the digestive tract, then, the gelatin capsule or tablet breaks up to release the microcapsules and the small microcapsules readily disperse. The gelatin microcapsule walls and the balm protectant act in concert to control the release of gastrointestinal irritant drug in the stomach. Thus, use of a microencapsular outer shell prevents contact of gastrointestinal irritant particles with the lining of the stomach but allows controlled release of the gastrointestinal irritant drug. The microencapsular wall is digested or dispersed in the intestine where the irritant/balm admixture is in a position to be readily dispersed by action of the salts and enzymes in the intestine. In this manner, it is possible to control the release of gastrointestinal irritant drug so that the possibility of ulceration is minimized and yet effective dosages of the pharmaceutical are achieved.

Accordingly, it is an object of the present invention to provide an improved controlled release product containing a gastrointestinal irritant drug and to provide methods for producing such a product.

Other objects and advantages of that invention will be apparent from the following description and the appended claims.

DESCRIPTION OF THE PREFERRED EMBODIMENTS

A preferred form of the controlled release pharmaceutical preparation of the present invention is a gelatin capsule filled with microcapsules having an irritant-/balm admixture as the core. Micronized potassium chloride is the preferred gastrointestinal irritant drug; although, as mentioned any solid, water soluble, micronized gastrointestinal irritant drug can be used. Preferably, the micronized potassium chloride particles have an average particle size of less than 10 microns.

In the preferred process, a slurry of micronized potassium chloride in a balm is prepared by admixing the micronized potassium chloride with the balm at a temperature above the melting point of the particular balm used. Preferred balm materials are either vegetable fats, such as glycerol mono vegetable shortening (which may be mixed with a lipid such as glyceryl monostearate to achieve the desired balm consistency), a petroleum jelly such as petrolatum, or waxes such as paraffin, beeswax or carnauba wax. Other vegetable fats, petroleum jellies, glycerol derivatives, waxes or mixtures thereof may also be used as the balm. The balm may be non-digestible as long as it is non-toxic, but preferred are digestible materials. Most preferred is combination of a wax mixture (such as paraffin, beeswax and carnauba wax) and glyceryl mono vegetable shortening. The balm should be heated to above its melting point so that the micronized potassium chloride can be easily and thoroughly admixed as a slurry.

The slurry is, then, preferably joined with a gelatin solution. A coacervating agent such as granulated potassium chloride is introduced to cause coacervation of the gelatin and microencapsulation of the potassium chloride/balm mixture.

Various other microencapsular wall materials may be used in place of gelatin. For example, a thin wall of cellulose acetate phthalate may be used. Likewise, various other coacervating agents may be used in place of potassium chloride. For example, sodium sulfate may be used.

In any event, the resulting microcapsules are hardened and dried to isolate a free-flowing microcapsule powder. The microcapsules can also be separated according to size. Preferred are microcapsules having an average diameter between about 100 and 1000 microns.

The microcapsules are preferably filled into a gelatin capsule. Alternatively, the microcapsules having the irritant/balm core may be tabletted. Known techniques can be used to do so. The usual binders, fillers, lubricants, etc. may be used for tabletting purposes. In use the capsule or tablet breaks up and disperses microcapsules throughout the stomach. The microencapsular wall will control the release of the gastroirritant drug in the stomach. Thereafter, the irritant/balm will emulsify, digest, or dissolve as it is dispersed in the intestinal tract.

Potassium chloride is thereby gradually released from the surface of the dispersing particles of irritant-/balm admixture. Localized areas of high potassium chloride concentration are avoided.

In another embodiment, the irritant/balm admixture need not be microencapsulated, but can be formed into microparticles. The microparticles may, then, be filled into a gelatin capsule or tabletted. As in the case of microencapsulation, a slurry of micronized gastrointestinal irritant drug in a melted balm is prepared. Again it is preferred that the balm be digestible; although, non-toxic non-digestible materials may also be used. In this instance the balm is preferably a solid material, a solid lipid, wax, or mixtures thereof. Most preferred is glyceryl monostearate. The slurry is dispersed in a medium, such as a gelatin solution containing surfactants, to form microparticles of balm containing micronized irritant. The microparticles are subsequently isolated, dried and filled into capsules or tabletted. In use, upon dissolution or dispersion of the capsule or tablet, the irritant balm microparticles will emulsify, digest, or dissolve after being dispersed in the digestive tract. The gastrointestinal irritant drug will slowly be released, and ulceration will be minimized because no large concentration of undissolved, unprotected drug is available to contact the lining of the digestive tract.

In order that the invention may be more readily understood, reference is made to the following examples, which are intended to illustrate the invention but are not to be taken as limiting the scope thereof.

EXAMPLE I

A balm was prepared by mixing 45.0 g Capmul GMVS, a glyceryl mono-vegetable shortening available from Capital City Products of Columbus, Ohio, with 15.0 g Capmul GMS-40, a glyceryl monostearate also available from Capital City Products. A slurry was made by admixing 60 g of the balm with 180 g of micronized potassium chloride and heating to 85° C. The slurry was poured into a solution of 15.0 g 300 bloom type A gelatin from General Foods Atlantic of Woburn, Mass. and 525 g water at 42° C. The mixture was stirred with a series 30 Lightnin' mixer in a one liter beaker while 150 g of granulated potassium chloride was added over a three minute period to cause coacervation and microencapsulation. The mixture containing the microcapsules was cooled to 15° C. Thereafter, 6.0 ml of 25% aqueous gluteraldehyde was added and the mixture heated to 28° C. The capsules were hardened for 4 hours, then washed twice with 500 ml water. Two teaspoons of Aerosil R 972, a hydrophobic silica powder from Degussa Corporation of Peterboro, N.J. were added and the microcapsules were dried for 4 hours on a 60 mesh screen in a fluidized bed drier.

The resulting product were microcapsules with a gelatin microencapsular wall and a potassium chloride/vegetable fat (i.e. irritant/semi-solid balm admixture) core. The percentage potassium chloride was determined to be 42% of the total microcapsule weight. The microcapsules had an average diameter of 800 microns and can, thus, be described as a powder.

EXAMPLE II

A slurry was formed by admixing 120.0 g of micronized potassium choride with 60 g of glycerol monostearate (Capmul-GMS-40) at 85° C. The slurry at 85° C. was poured into a solution of 10.0 g, 300 Bloom type A gelatin, 350 g water at 40° C. stirred with a series 30 Lightnin' mixer in a one liter beaker. The gelatin solution was decanted. The particles were washed with 500 ml water, filtered, and dried in a fluidized bed drier at room temperature.

The resulting product was 300-1000 micron microparticle of potassium chloride/lipid (i.e. irritant-/solid balm admixture). The percentage potassium chloride was determined to be 50% of the total weight. The microparticles so prepared can be considered a powder.

600 mg of the powder was filled into a number 000 gelatin capsule. The resulting per capsule dosage was determined to be 5.0 milli-equivalents of potassium.

EXAMPLE III

A balm was prepared by admixing 60.0 g paraffin (MP 52°-54° C.), 17.5 g beeswax, 15 g. carnauba wax, and 7.5 g. Capmul GMVS, a glyceryl mono-vegetable shortening from Capital City Products of Columbus, Ohio, at 100° C. 400 g. micronized KCl was mixed into the balm to form a slurry. The slurry at 100° C. was dispersed into a 60° C. solution of 125 g. 200 Bloom type A gelatin (Milligan and Higgins, Chicago, Ill. in 1250 ml water containing five ml Naccanol surfactant (Stepan Company, Northfield, Ill.) in a 4 liter Waring blender set on high speed and controlled at 30 volts by a Variac. Immediately after dispersion of the slurry, ice was added to cool the mixture to 30° C. The gelatin solution was decanted. The particles were then added to a solution of 25 g., 300 Bloom type A gelatin (General Foods Atlantic) in 875 ml water at 50° C. slowly stirred with a lightnin' mixer. 400 g. granulated potassium chloride was added over a three minute period to induce coacervation and cause microencapsulation. Ice was added to chill the mixture to 20° C. Thereafter, 10 ml of 25% gluteraldehyde was added and the microcapsules were hardened for 16 hours at 25° C. The liquid was decanted. The microcapsules were washed twice with 500 ml water, then filtered. Approximately 50 ml of Aerosil R972 were added and the microcapsules were dried for four hours in a fluidized bed drier. At 25° C. the resulting microcapsules were determined to contain 57% potassium chloride.

EXAMPLE IV

A balm was prepared by admixing 96 gm paraffin (MP 52°-54° C.), 24 gm beeswax, 32 gm carnauba wax and 8 gm capmul GMVS, a glyceryl mono-vegetable shortening from Capital City Products of Columbus. 640 gm of micronized potassium chloride was mixed into the balm to form a slurry. The slurry at 100° C. was dispersed into a 60° C. solution of 150 gm 200 bloom type A gelatin (Milligan and Higgins, Chicago, Ill. in 1500 ml water containing 10 ml Naccanol surfactant (Stepan Company, Northfield, Ill. in a 4 liter Waring Blender set on high speed and controlled at 31 volts by a variac. Immediately after dispersion of the slurry the stirring was stopped and the gelatin solution was decanted. The particles were added to a solution of 30 gm 300 bloom, type A gelatin (General Foods Atlantic) in 1 liter water at 50° C. 450 gm granulated KCl was added over a 2 minute period to induce coacervation and cause microencapsulation. Ice was added to chill the mixture to 20° C. Thereafter 10 ml of 25% gluteraldehyde was added and the microcapsules were hardened for 16 hours at 25° C. The liquid was decanted. The microcapsules were washed twice with 500 ml water, then filtered. Approximately 50 ml of aerosil R972 were added and the microcapsules were dried for four hours in a fluidized bed drier at 25° C. The resulting microcapsules were determined to contain 65% potassium chloride.

DISSOLUTION STUDIES

Table I shows that the dissolution rate of potassium chloride from the microcapsules of examples I and III can be controlled by varying the composition of the balm. In this case, the dissolution rate increases as the fraction of GMVS (glyceryl mono-vegetable shortening) in the balm increases.

TABLE I

| | Percent Dissolved | | |
|---|---|---|---|
| Time | Example I | Example III | Example IV |
| 1 hr. | 70 | 23 | 17 |
| 2 hrs. | 78 | 34 | 29 |
| 3 hrs. | 89 | 55 | 41 |
| 4 hrs. | 89 | 63 | 51 |
| 5 hrs. | 89 | 72 | 60 |

ANIMAL STUDIES

The potassium chloride dosage forms prepared in Examples II were tested for gastrointestinal irritation in pigs in a study using Ciba Slow K as a positive control. In the study four 10 Kg pigs were dosed with the test materials and four pigs were dosed with Ciba Slow K wax matrix tablets at 1800 mg KCl b.i.d. for four days. On the fifth day the pigs were sacrificed and subject to gross examination of the major structures of the gastrointestinal tract. As shown in Table II the microparticles of Example II dramatically reduce the incidence of gastrointestinal irritation when compared to wax matrix tablets.

TABLE II

| | EXAMPLE II | | | CIBA SLOW K | | |
|---|---|---|---|---|---|---|
| | Reddened | Swollen | Corroded | Reddened | Swollen | Corroded |
| Esophagus | 0/4 | 0/4 | 0/4 | 0/4 | 0/4 | 0/4 |
| Stomach | 3/4 | 3/4 | 1/4 | 3/4 | 3/4 | 3/4 |
| Duodenum | 2/4 | 0/4 | 1/4 | 4/4 | 0/4 | 3/4 |
| Jejunum | 2/4 | 0/4 | 0/4 | 3/4 | 1/4 | 2/4 |
| Ileum | 1/4 | 0/4 | 0/4 | 2/4 | 0/4 | 1/4 |
| Ileo-Cecal Orifice | 1/4 | 1/4 | 0/4 | 2/4 | 1/4 | 2/4 |
| Colon | 3/4 | 1/4 | 0/4 | 4/4 | 1/4 | 1/4 |
| Rectum | 0/4 | 0/4 | 0/4 | 2/4 | 0/4 | 1/4 |

In another study the potassium chloride dosage form prepared in Example IV was tested for gastrointestinal irritation in pigs using A. H. Robbins Micro X Extend caps and Mead Johnson's Klotrix as positive controls. In this study four 10 Kg pigs were dosed with the test material and four pigs were dosed with Micro K and Klotrix at 2400 mg KCl b.i.d. for four days. On the fifth day the pigs were sacrificed and subjected to gross examination of the major structures of the gastrointestinal tract. As shown in Table III the microcapsules of Example IV dramatically reduce the incidence of gastrointestinal irritation when compared to tablets containing a permanent erosion resistant polymer film coating over a core of potassium chloride in a wax-like matrix (Klotrix) and when compared to controlled release microencapsulated potassium chloride in a gelatin capsule (Micro K Extend caps). Most significantly, the microcapsules of Example IV produced only 1 corrosion in the group of 4 pigs whereas Klotrix and Micro K extend caps each provided 5 corrosions in their groups of 4 pigs. The microcapsules of Example IV also have a greater bid-availability of potassium than Klotrix or Micro K extend caps as demonstrated by the increases in urine potassium output.

While the products and methods herein described

TABLE III

| | Example IV | | | A. H. Robbins Micro K Extend Caps | | | Mead Johnson Klotrix | | |
|---|---|---|---|---|---|---|---|---|---|
| | Reddened | Swollen | Corroded | Reddened | Swollen | Corroded | Reddened | Swollen | Corroded |
| Esophagus | 0/4 | 0/4 | 0/4 | 0/4 | 0/4 | 0/4 | 0/4 | 0/4 | 0/4 |
| stomach | 2/4 | 0/4 | 0/4 | 1/4 | 0/4 | 1/4 | 0/4 | 0/4 | 2/4 |
| Duodenum | 1/4 | 0/4 | 1/4 | 0/4 | 0/4 | 4/4 | 0/4 | 0/4 | 3/4 |
| Jejunum | 0/4 | 0/4 | 0/4 | 0/4 | 0/4 | 0/4 | 0/4 | 0/4 | 0/4 |
| Ileum | 0/4 | 0/4 | 0/4 | 0/4 | 0/4 | 0/4 | 0/4 | 0/4 | 0/4 |
| Ileo-Cecal Orifice | 0/4 | 0/4 | 0/4 | 0/4 | 0/4 | 0/4 | 0/4 | 0/4 | 0/4 |
| Colon | 0/4 | 0/4 | 0/4 | 0/4 | 0/4 | 0/4 | 0/4 | 0/4 | 0/4 |
| Rectum | 0/4 | 0/4 | 0/4 | 0/4 | 0/4 | 0/4 | 0/4 | 0/4 | 0/4 |
| Urine Potassium Average Increase | 240.5 meq/liter | | | 141.6 meq/liter | | | 82.5 meq/liter | | | constitute preferred embodiments of the invention, it is to be undestood that the invention is not limited to these precise products and methods, and that changes may be made therein without departing form the scope of the invention:

What is claimed is:

1. A pharmaceutical preparation comprising microparticles of an admixture of micronized gastrointestinal irritant drug having an average particle size of less than 10 microns in a non-toxic, protective balm which is readily dispersible throughout the digestive tract whereby said micronized gastrointestinal irritant drug is embedded in said balm and coated by it and is dissolvable in a controlled manner by the digestive fluids upon dispersion of said balm, said microparticles having an average diameter of between about 100 and 1000 microns.

2. The pharmaceutical preparation of claim 1 wherein said gastrointestinal irritant drug is micronized potassium chloride.

3. The pharmaceutical preparation of claim 2 wherein said balm is selected from the group consisting of digestible or nondigestible lipids, waxes, and mixtures thereof.

4. The pharmaceutical preparation of claim 3 wherein said microparticles are placed in a capsule.

5. The pharmaceutical preparation of claim 4 wherein said capsule is a gelatin material.

6. A pharmaceutical preparation comprising microcapsules having a microencapsular wall and a core of an admixture of micronized gastrointestinal irritant drug having an average particle size of less than 10 microns in a non-toxic, protective balm which is readily dispersible throughout the intestinal tract whereby said micronized gastrointestinal irritant drug is embedded in said balm and coated by it and is dissolvable in a controlled manner by the digestive fluids upon dispersion of said balm, said microcapsules having an average diameter of between about 100 and 1000 microns.

7. The pharmaceutical preparation of claim 6 wherein said gastrointestinal irritant drug is micronized potassium chloride.

8. The pharmaceutical preparation of claim 7 wherein said balm is selected from the group consisting of digestible or nondigestible semi-solid vegetable fats, petroleum jellies, waxes, lipids, glycerol derivatives, and mixtures thereof.

9. The pharmaceutical preparation of claim 8 wherein said balm is a mixture of a solid lipid or wax and a vegetable fat.

10. The pharmaceutical preparation of claim 9 wherein said microcapsular wall is gelatin.

11. The pharmaceutical preparation of claim 10 wherein said microcapsules are placed in a gelatin capsule.

* * * * *